United States Patent [19]

Siddiqi et al.

[11] Patent Number: 4,769,332

[45] Date of Patent: Sep. 6, 1988

[54] METHOD AND COMPOSITION FOR ENHANCEMENT OF GROWTH OF MYCOBACTERIA

[75] Inventors: Salman H. Siddiqi, Timonium; Rodney L. Broman, Fallston, both of Md.

[73] Assignee: Becton Dickinson and Company, Franklin Lakes, N.J.

[21] Appl. No.: 773,740

[22] Filed: Sep. 6, 1985

Related U.S. Application Data

[63] Continuation-in-part of Ser. No. 548,476, Nov. 3, 1983, abandoned.

[51] Int. Cl.$^4$ ............................................. C12N 1/38
[52] U.S. Cl. .................................... 435/244; 435/253; 435/863
[58] Field of Search ..................... 435/244, 863, 253

[56] References Cited

U.S. PATENT DOCUMENTS 3,293,145 12/1966 Leavitt et al. ........................ 435/244

OTHER PUBLICATIONS

Difco Manual, 9th Ed., Difco Laboratories Inc., Detroit, Mich., 1977, pp. 104–110 and 274–275.
Saito et al., (1983), Journal of Bacteriology, vol. 153, No. 3, pp. 1294–1300.

*Primary Examiner*—Sam Rosen
*Attorney, Agent, or Firm*—James R. McBride

[57] ABSTRACT

A growth medium for mycobacteria is provided which has enhanced growth properties. The growth medium contains an effective amount of polyoxyethylene stearate and an albumin.

11 Claims, 1 Drawing Sheet

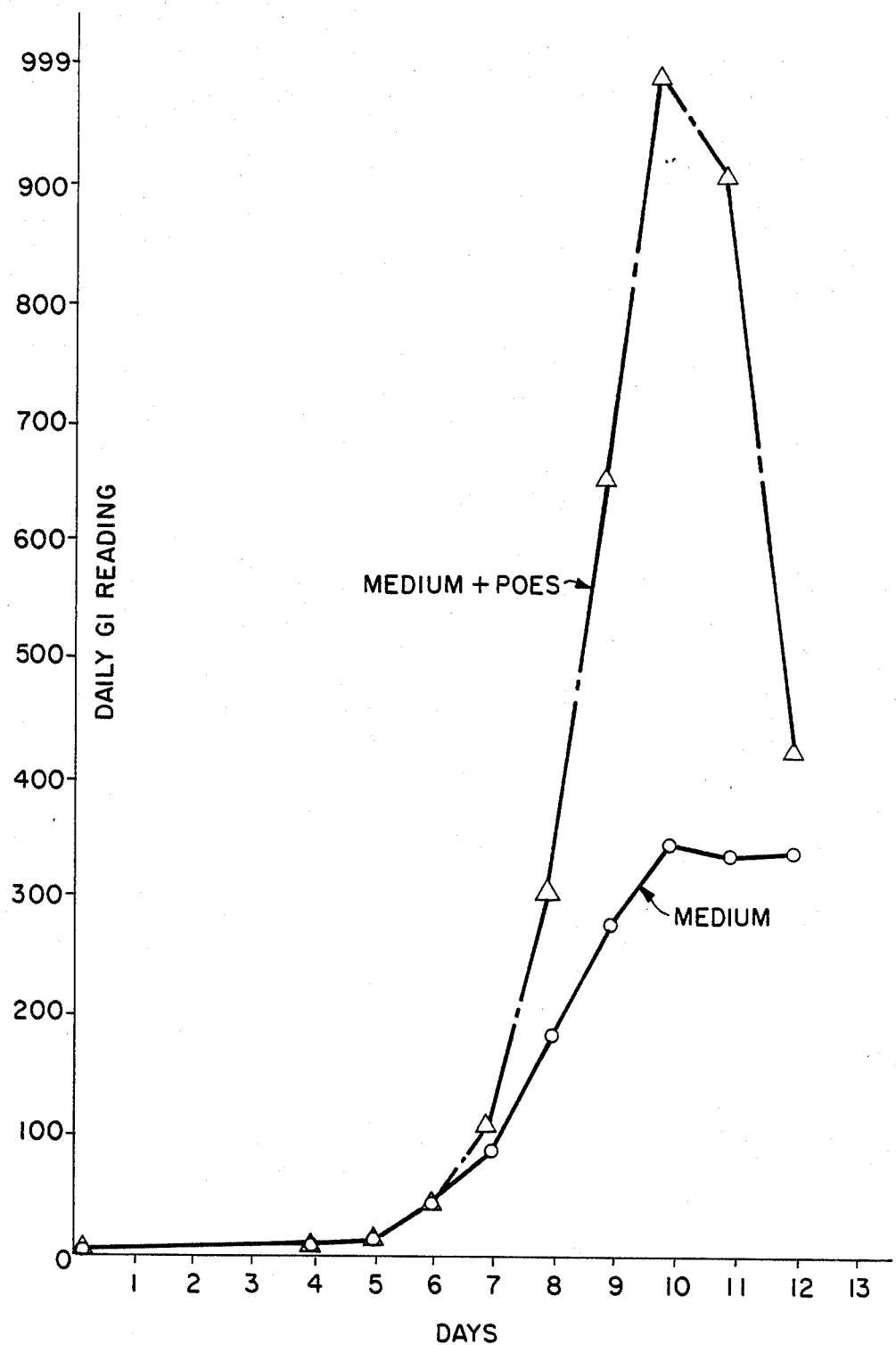

METHOD AND COMPOSITION FOR ENHANCEMENT OF GROWTH OF MYCOBACTERIA

The present application is a continuation-in-part of U.S. patent application Ser. No. 548,476, filed Nov. 3, 1983, now abandoned.

The present invention relates generally to a method and composition for enhancing the growth rate and amount of growth of mycobacteria in a growth medium. More particularly, the present invention describes a composition and method for the enhancement of the growth and amount of growth of mycobacteria in a suitable bacterial growth medium.

BACKGROUND OF THE INVENTION

The cultivation of propagating microorganisms by providing the proper nutritional and environmental conditions is well known. In general, the contributing factors for suitable propagating conditions include the nature and level of nutrients provided in the growth media, pH, temperature, and aeration. Other factors which must be controlled include the salt concentration and osmotic pressure of the medium and in some cases, such special factors as light for photosynthetic organisms.

A suitable growth medium must contain all the nutrients required by the microorganism which is to be cultivated. In general, the following nutrients must be provided:

(1) hydrogen donors and acceptors;
(2) a carbon source;
(3) a nitrogen source;
(4) minerals, such as sulphur and phosphorous and trace elements such as potassium, magnesium, calcium and iron.

In addition, it is known that certain growth factors are required. A growth factor is an organic compound which a microorganism must contain in order to grow but which is unable to synthesize. Many microorganisms, when provided with the nutrients listed above, are able to synthesize all of the organic constituents of their protoplasm, including amino acids, vitamins, purines and pyrimadines, fatty acids and other compounds. Each of these essential compounds is synthesized by a discrete sequence of enzymatic reactions and each enzyme is produced under the control of a specific gene. When an organism undergoes a gene mutation resulting in failure of one of these enzymes to function, the chain is broken and the end product is no longer produced. The microorganism must then obtain that compound from the environment and the compound has become a growth factor for the organism.

U.S. Pat. No. 3,293,145 to Leavitt describes a method for increasing the growth rate of achromobacter and Nocardia, comprising incubating the microorganisms in the presence of oxygen and an aliphatic hydrocarbon such as polyoxyethylene stearate, as the sole source of carbon for energy and growth. The hydrocarbon is added to an aqueous mineral salt solution which includes 0.015 to 10% of urea, 0.01 to 10% of a water soluble inorganic ammonium salt and 0.001 to 5% of a nonionic surface active agent.

Different microorganisms vary widely in their nutritional and growth factor requirements. The present invention is directed to the provision of a substance which enhances the growth rate and amount of growth of mycobacteria in a growth medium containing nutrients required for their growth.

SUMMARY OF THE INVENTION

It has been determined that the addition of polyoxyethylene stearate to a growth medium containing nutrients for Mycobacteria enhances the growth rate and amount of growth of Mycobacteria in a liquid medium. In addition to the increase in growth, as observed visually or on stained smear, the enhancement can be observed by a higher $CO_2$ production which is significant for detection of the growth of Mycobacteria in an automated radioimmunoassay systems.

DESCRIPTION OF THE DRAWINGS

The single FIGURE is a graph of a growth medium used to grow a strain of *M. tuberculosis.* The growth medium is designated BACTEC 12A. The lower line of the graph shows the use of the 12A medium by itself. The upper line of the graph shows the use of the 12A medium in combination with polyoxyethylene stearate.

DETAILED DESCRIPTION OF THE INVENTION

Mycobacteria in general, and *M. tuberculosis* and *M. bovis* in particular, are fastidious microorganisms which are very slow growing. It takes about two to three weeks to grow these organisms on the culture media conventionally used. There have been several efforts to find a medium or a substance which can enhance the growth and reduce the time factor. A report on the stimulating effect of RNA on the growth of mycobacteria has resulted in the Gruft modification of Lowenstein Jensen medium (Gruft, H. 1971, Isolation of Acid-Fast Bacilli From Contaminated Specimens, Health lab Science 8:79). The enhancement of growth by RNA, however, is still questionable and there has been no demonstration of any significant effect through the use of such RNA addition to the growth medium.

A method for detecting bacteria using the detection of radioactive $^{14}CO_2$ is described in U.S. Pat. No. 3,935,073 to Waters. A growth medium to be used along with the apparatus described in the Waters patent and which is suitable for the culture of Mycobacteria contains the following nutrients at the indicated level:

| | |
|---|---|
| 7H9 broth base (containing potassium and sodium phosphates, sodium glutamate, sodium citrate, ammonium sulphate, pyridoxine, ferric ammonium citrate, magnesium sulphate, zinc sulphate, copper sulfate, biotin and calcium chloride obtained from BBL Microbiology Systems in Cockeysville, Maryland) | 0.47% |
| Bovine serum albumin | 0.5% |
| Caseine Hydrolysate | 0.1% |
| Catalase | 96 units/vial |
| $^{14}C$ labelled substrate | 2 uCi/vial |
| Deonized water | balance to 2 ml |
| Final pH | 6.8 ± 0.1 |

Albumin is an essential carbon source in a medium used for the growth of mycobacteria. Albumin is a simple protein found in nearly every animal and in many vegetable tissues. Albumins are characterized as being soluble in water and coagulable by heat. They contain carbon, hydrogen, nitrogen, oxygen and sulphur. A preferred albumin for the growth media of the present invention is bovine serum albumin. The albumin is preferably present in the growth media at a level of from about 0.1 percent by weight to about 1.0 percent by weight.

The addition of polyoxyethylene stearate to a growth media for mycobacteria containing albumin apparently provides a synergistic effect as compared to the use of albumin alone. Mycobacteria cannot be grown in a growth media containing polyoxyethylene but which does not also contain albumin. The use of other carbon sources in the growth media (such as casein hydrolysate) is optional. In general, polyoxyethylene stearate is added to the growth medium in a concentration of from about 10 micrograms to about 10,000 micrograms per milliliter of medium. The enhancement is directly proportional to the concentration of polyoxyethylene stearate. In particular, it is found that from about 50 to about 500 micrograms per milliliter of polyoxyethylene stearate is a preferred range at which the growth and production of $^{14}CO_2$ is enhanced without having any negative effect on the acid fastness or other physiological properties of the organisms.

Polyoxyethylene stearate solubilizes in an aqueous growth medium. Consequently the physical form of the polyoxyethylene stearate is not critical. The polyoxyethylene stearate can be added in the form of pellets, granules or powder or can be sprayed onto the interior surface of a culture vial.

As an example of the growth enhancement properties of the method and composition of the present invention, a growth medium was prepared having the following components at the indicated level:

| | |
|---|---|
| 7H9 broth base | 0.47% |
| Bovine serum albumin | 0.5% |
| Caseine Hydrolysate | 0.1% |
| Catalase | 96 units/vial |
| $^{14}C$ labelled substrate | 2 uCi/vial |
| Deonized water | balance to 2 ml |
| Final pH | 6.8 ± 0.1 |

The growth medium described above was divided into two portions. In one-half, polyoxyethylene stearate (granular form) was added at a level of one hundred micrograms per milliliter. The other half of the growth medium was used without any further additions.

A suspension of *M. tuberculosis,* strain H37Rv, equivalent to MacFarland No. 1 standard, was diluted 1:500 and 0.1 ml was inoculated into each bottle containing 2 ml of growth medium. Eight bottles each of the growth medium alone and the growth medium plus the polyoxyethylene stearate were inoculated. All of the bottles were read on an apparatus similar to that described in the Waters patent previously mentioned. The readings were taken daily for twelve days. The daily growth index (GI) values recorded by the apparatus indicated the $^{14}CO_2$ production from the $^{14}C$-labelled substrate present in the medium. The results of the readings were used to prepare the two plots of FIG. 1.

The growth of *M. tuberculosis* was also observed visually as well as by making smears and staining by the Ziehl Neelsen method for acid-fast bacteria.

It is evident from the plots of FIG. 1 that the growth curve of *M. tuberculosis* in the growth medium to which polyoxyethylene stearate has been added is significantly enhanced from that of the growth medium without such addition. The enhancement effect on the growth of *M. tuberculosis* in the medium is clearly shown once the growth index reaches around 100–150 on day 6 through day 8. At this point, the increase in mycobacterial growth becomes very abrupt. At an equivalent growth index reading, the amount of growth, as observed visually, is also significantly higher in the polyoxyethylene containing medium than the regular 12A medium. When smears are prepared from the growth medium containing polyoxyethylene stearate and stained by the Ziehl Neelsen method, acid-fast bacteria are more dispersed in long ropey serpentine cords and there are more in number.

Data of primary isolation (recovery) of mycobacteria from clinical specimens (sputum) shows enhancement of growth and GI output of a positive mycobacterial culture in the presence of polyoxyethylene stearate. After the day 7 GI output, which also indicates the rate and amount of growth, is significantly higher in the 12A medium with polyoxyethylene stearate as compared to 12A medium without it.

Similar enhancement effect has been noticed with *M. bovis* and many mycobacteria other than *M. tuberculosis* (MOTT or atypical mycobacteria).

What is claimed is:

1. A method for the enhancement of growth of mycobateria comprising adding a mycobateria to an aqueous culture medium containing an effective amount of polyoxyethylene stearate and an albumin and subjecting the culture medium to conditions suitable for growth of the mycobacteria.

2. A method in accordance with claim 1 wherein said polyoxyethylene stearate is added to said culture medium at a level of from about 10 to about 10,000 micrograms per milliliter of medium.

3. A method in accordance with claim 1 wherein said polyoxyethylene stearate is added to said culture medium at a level of from about 50 to about 500 micrograms per milliliter of medium.

4. A method in accordance with claim 1 wherein said albumin is present at a level of from 0.1 to about 1.0% by weight.

5. A method in accordance with claim 1 wherein said albumin is bovine serum albumin.

6. A method in accordance with claim 1 wherein said mycobacteria is *M. tuberculosis.*

7. A method in accordance with claim 1 wherein said mycobacteria is *M. bovis.*

8. A growth medium having enhanced growth properties for mycobacteria comprising a culture medium containing an effective amount of polyoxyethylene stearate and an albumin.

9. A growth medium in accordance with claim 8 wherein said polyoxyethylene stearate is added to said culture medium at a level of from about 10 to about 10,000 micrograms per milliliter medium.

10. A growth medium in accordance with claim 8 wherein said polyoxyethylene stearate is added to said culture medium at a level of from about 50 to about 500 micrograms per milliliter.

11. A growth medium in accordance with claim 8 wherein said albumin is present at a level of from about 0.1 to about 1.0% by weight.

* * * * *